US008219570B2

(12) United States Patent
Crucs

(10) Patent No.: US 8,219,570 B2
(45) Date of Patent: Jul. 10, 2012

(54) SYSTEM AND METHOD FOR THE AUTOMATIC GENERATION OF A QUERY TO A DICOM SERVER

(75) Inventor: Kevin M. Crucs, Akron, OH (US)

(73) Assignee: Apteryx, Inc., Akron, OH (US)

( * ) Notice: Subject to any disclaimer, the term of this patent is extended or adjusted under 35 U.S.C. 154(b) by 1902 days.

(21) Appl. No.: 11/125,930

(22) Filed: May 10, 2005

(65) Prior Publication Data
US 2006/0259463 A1 Nov. 16, 2006

(51) Int. Cl.
*G06F 17/30* (2006.01)
*G06Q 50/00* (2012.01)

(52) U.S. Cl. .......................................... 707/758; 705/2
(58) Field of Classification Search .................. 707/102, 707/104, 758
See application file for complete search history.

(56) References Cited

U.S. PATENT DOCUMENTS

| 6,859,288 | B1 | 2/2005 | Brackett et al. | |
|---|---|---|---|---|
| 7,860,725 | B2 * | 12/2010 | Gopinathan et al. | 705/2 |
| 2002/0055917 | A1 * | 5/2002 | Muraca | 707/1 |
| 2004/0210319 | A1 * | 10/2004 | Lapstun et al. | 700/1 |
| 2004/0249677 | A1 * | 12/2004 | Datta et al. | 705/3 |
| 2005/0150944 | A1 * | 7/2005 | Melick et al. | 235/375 |
| 2006/0173713 | A1 * | 8/2006 | Petro et al. | 705/2 |
| 2006/0242148 | A1 * | 10/2006 | Rothpearl et al. | 707/7 |

OTHER PUBLICATIONS

DICOM Modality Worklist: An Essential Component in a PACS Environment, dated Aug. 2000.*

* cited by examiner

*Primary Examiner* — Tarek Chbouki
(74) *Attorney, Agent, or Firm* — Hahn Loeser & Parks LLP

(57) ABSTRACT

A system and method for automatically generating a query to a DICOM server are disclosed. The system comprises patient identification information encoded in a tangible medium. The system further comprises a reading device to read the encoded patient identification information from the tangible medium. The system also includes a computer-based platform hosting a medical software application. The computer-based platform operationally interfaces to the reading device to receive the read patient identification information from the reading device and to automatically generate a DICOM query, using the medical software application, such that the DICOM query includes at least a portion of the patient identification information. The system further comprises at least one DICOM server operationally interfacing to the computer-based platform to receive the DICOM query from the computer-based platform.

20 Claims, 8 Drawing Sheets

SYSTEM AND METHOD FOR THE AUTOMATIC GENERATION OF A QUERY TO A DICOM SERVER

TECHNICAL FIELD

Certain embodiments of the present invention relate to submitting queries to a DICOM server. More particularly, certain embodiments of the present invention relate to a system and method to use encoded information to automatically generate and submit queries to a DICOM server.

BACKGROUND OF THE INVENTION

Digital Imaging and Communications in Medicine (DICOM) is a well-known standard for transferring images and associated information between devices manufactured by various vendors. Typically, a DICOM server is used to store, organize, and manage medical images. Various external systems may desire to communicate with a DICOM server to store images to the DICOM server and/or to retrieve images from the DICOM server by submitting queries to the DICOM server.

However, the DICOM standard provides for more than the transferring and storing of digital medical images. Other DICOM functions include media storage, query/retrieve, worklist query, make image hard copies, study and results management, print management, worklist management, and test connectivity verification.

A basic concept used in the DICOM standard is that of "Services on Objects". An example of an "object" is an X-ray image. Two examples of a "service" are the "query/retrieve" and "store" functions. In the DICOM standard, processes of operating on objects are called "Service Object Pair Classes" (SOP Classes). Examples of SOP Classes include "store an X-ray image", "print an X-ray image", and "retrieve a worklist".

Unique Identifiers (UID's) are determined for SOP classes and are also applied to studies, series, and images. A patient study includes a study component such as, for example, an examination using a particular type of medical imaging machine. The images that are captured in sequence during the study on a patient form a series of objects.

The DICOM standard is founded on a client/server concept. A device that uses a service is the client device, and the device that provides the service is the server device. The client device is called a Service Class User (SCU). The server device is called a Service Class Provider (SCP). An SCU transmits a Service Request to an SCP over a network. The SCP transmits back a response to the SCU over the network. For information to be transferred between a SCP and a SCU, a communication syntax must be agreed upon an association between the SCU and the SCP must be opened.

The DICOM standard facilitates communication of digital medical images of various types including X-ray, computerized tomography, magnetic resonance, and ultrasound, for example. DICOM activities are administered in a queued manner via application software running on a host computer. The host computer may be an integral part of a medical imaging machine.

Typically, a client user has to manually enter patient information into data fields of an application window to serve as search terms for a query. Such manual entry of patient information is inefficient and prone to errors.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY OF THE INVENTION

An embodiment of the present invention provides a method to automatically generate a query to a DICOM server. The method includes reading patient identification information using a bar code scanning device. The patient identification information is encoded in a bar code on, for example, a patient identification card belonging to a patient. The method further includes automatically forwarding the read patient identification information from the bar code scanning device to a medical software application on a computer-based platform. A DICOM query operation is then initiated to search at least one DICOM server, based at least on a portion of the patient identification information, using the medical software application.

Another embodiment of the present invention comprises a system for automatically generating a query to a DICOM server. The system comprises an encoded medium including encoded patient information of a patient. The system further comprises a reading device to read the patient identification information encoded in the encoded medium. The system also comprises a computer-based platform hosting a medical software application. The computer-based platform operationally interfaces to the reading device to receive the read patient identification information from the reading device and to automatically generate a DICOM query, using the medical software application. The DICOM query includes at least a portion of the patient identification information. The system further includes at least one DICOM server operationally interfacing to the computer-based platform to receive the DICOM query from the computer-based platform, for example, over a network.

A further embodiment of the present invention provides a method to automatically generate a query to a DICOM server. The method includes reading patient identification information using a reading device, wherein the patient identification information is encoded on a tangible medium. The method further includes automatically forwarding the read patient identification information from the reading device to a medical software application on a computer-based platform. The method also includes initiating a DICOM query operation to search at least one DICOM server, based at least one a portion of the patient identification information, using the medical software application.

These and other advantages and novel features of the present invention, as well as details of an illustrated embodiment thereof, will be more fully understood from the following description and drawings.

DETAILED DESCRIPTION OF THE INVENTION

Figure 1:
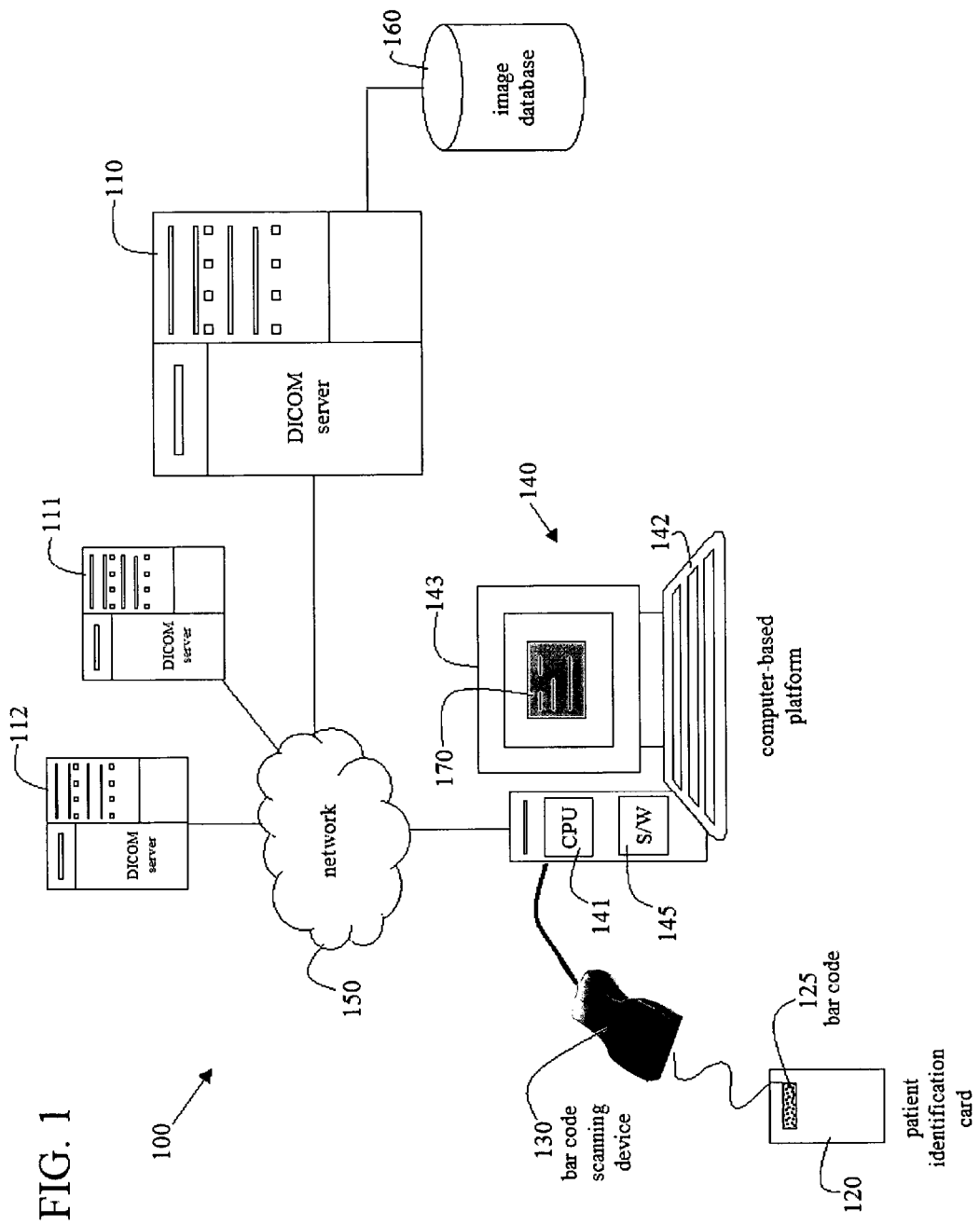
FIG. 1 is a schematic block diagram of a first exemplary embodiment of a system for automatically generating a query to a DICOM server, in accordance with various aspects of the present invention.

FIG. 1 is a schematic block diagram of an exemplary embodiment of a system 100 for automatically generating a query to a DICOM server (e.g, 110), in accordance with various aspects of the present invention. The system 100 includes a patient identification card 120 belonging to a medical patient. The patient identification card includes a bar code 125 with encoded patient identification information. The patient identification information may include, for example, the patient's name, a patient identification number, the patient's sex (male or female), the patient's date of birth, and the patient's age. Other identification information is possible as well (e.g., insurance information), in accordance with various embodiments of the present invention. The patient identification card 120 is typically the same size and shape as a standard credit card. However, other sizes and shapes are possible as well, in accordance with various embodiments of the present invention.

In accordance with alternative embodiments of the present invention, the patient identification card 120 may be, instead, a medical file folder, or a hard copy of a medical image or images, for example, having a bar code printed thereon. Other tangible media may be used as well, to include a bar code with encoded patient identification information.

The system 100 further includes a bar code scanning device 130 to read the patient identification information encoded in the bard code 125. The bar code scanning device 130 may be a wand type of device that is held in a user's hand and waved across the bar code 125 of the patient identification card 120. Alternatively, the bar code scanning device 130 may be a stationary device where the patient identification card 120 is waved across the stationary bar code scanning device 130 for reading. Other bar code scanning device implementations are possible as well, in accordance with various embodiments of the present invention. For example the bar code scanning device 130 may include a slot that the patient identification card 120 may be inserted into for reading of the bar code 125.

Figure 7:
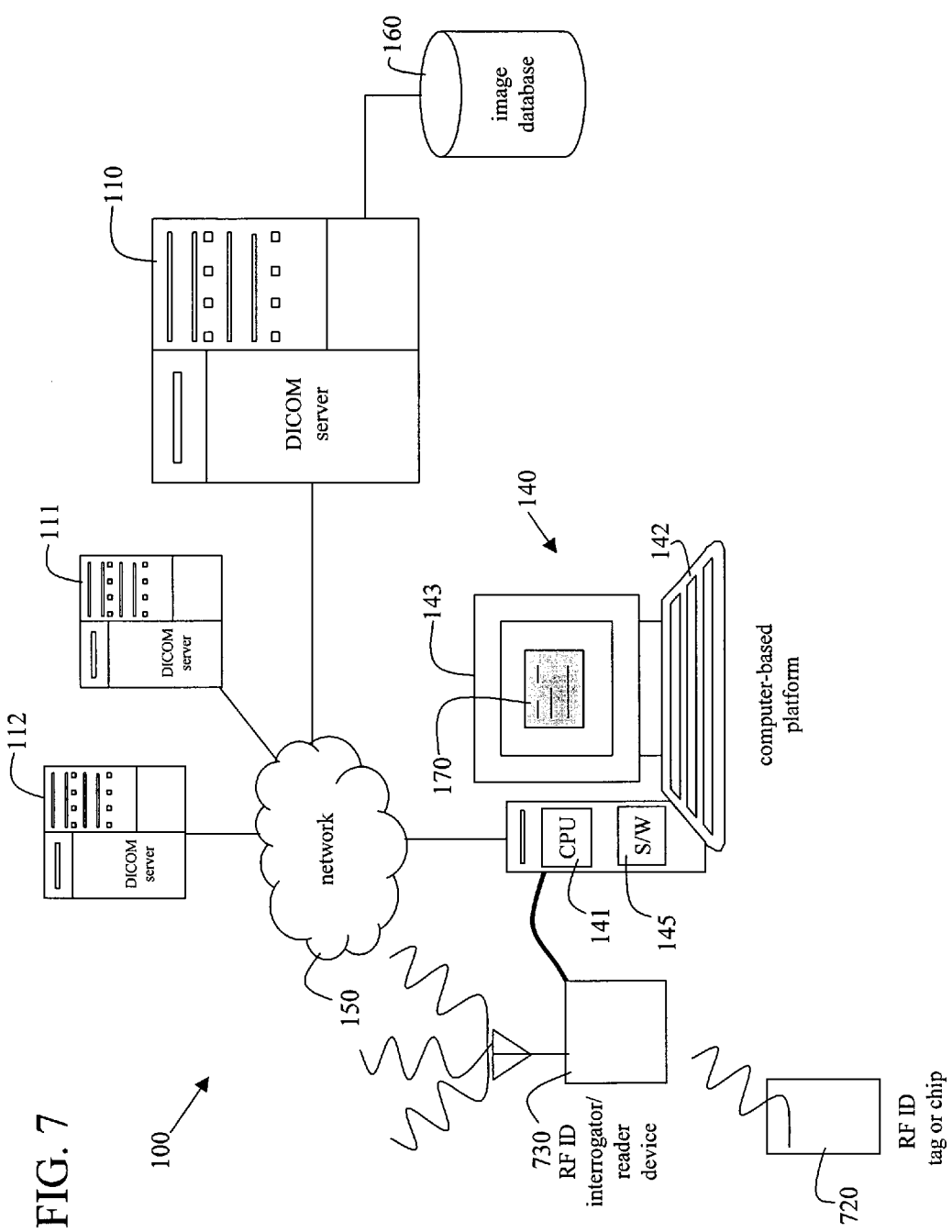
FIG. 7 is a schematic block diagram of a second exemplary embodiment of a system for automatically generating a query to a DICOM server, in accordance with various aspects of the present invention.

As an alternative to a bar code scanning device 130, the system 100 may instead use a radio frequency (RF) identification (ID) interrogator/reader device 730 as shown in FIG. 7. Also, instead of having a bar code printed on a tangible medium, patient identification information is encoded in an RF ID tag or chip 720 as shown in FIG. 7. The RF ID interrogator/reader device 730 is used to interrogate the RF ID tag 720 such that the RF ID tag 720 transmits the encoded patient identification information back to the RF ID interrogator/reader device 730. Other reading devices and encoded medium are possible as well, in accordance with various alternative embodiments of the present invention.

The system 100 also includes a computer-based platform 140 hosting a medical software application 145. The computer-based platform 140 operationally interfaces (wired or wirelessly) to the bar code scanning device 130 (or some other reading device such as, for example, the RF ID interrogator/reader device 730) to receive the read patient identification information from the bar code scanning device 130 (or other reading device). The computer-based platform 140 may comprise, for example, a personal computer (PC), a work station, or a medical imaging machine, in accordance with various embodiments of the present invention. For example, a medical imaging machine may comprise an ultrasound machine, an X-ray machine, a magnetic resonance (MR) machine, or any other type of medical imaging machine. Other computer-based platforms are possible as well, in accordance with other embodiments of the present invention. A typical computer-based platform, in accordance with certain embodiments of the present invention, includes a central processing unit 141 (CPU), a user interface 142 (e.g., a keyboard and a mouse), and a display 143 (e.g., a CRT monitor or a flat-panel display). In accordance with an embodiment of the present invention, the bar code scanning device 130 (or other reading device) may be an integral part of the computer-based platform 140.

The medical software application 145 may comprise, for example, a patient management software application or an imaging software application, in accordance with various embodiments of the present invention. The medical software application 145 uses at least a portion of the read patient identification information to generate a DICOM query (e.g., a worklist query or a query/retrieve). A DICOM query operation may be performed by the system 100 to access a worklist for the patient, to retrieve digital image files corresponding to the patient, or to retrieve other digital medical files or data objects associated with the patient (e.g., a medical study or report file).

The system 100 further includes at least one DICOM server (e.g., 110-112) operationally interfacing (wired or wirelessly) to the computer-based platform 140 via at least one network 150. The DICOM servers 110-112 are used to digitally store, organize, and control access of patient files including worklists, digital images, medical reports, or any other type of digital medical file. Such digital patient files may be stored directly in memory of the DICOM server itself or in a storage medium that operationally interfaces to the DICOM server. For example, the system 100 also includes an image database 160 operationally interfacing (wired or wirelessly) to the DICOM server 110. The image database is used to store digital medical images of patients. Also, the DICOM servers 110-112 may be used to digitally store, organize, and control access of data objects associated with patients. In general, as used herein, a DICOM server comprises a device that provides a service to a client device (e.g., the computer-based platform 140).

The network 150 may include at least one of a local area network (LAN), a wide area network (WAN), and a global informational network such as, for example, the Internet, in accordance with various embodiments of the present invention. The network 150 may be wired, wireless, or a combination of wired and wireless, in accordance with various embodiments of the present invention.

Figure 2:
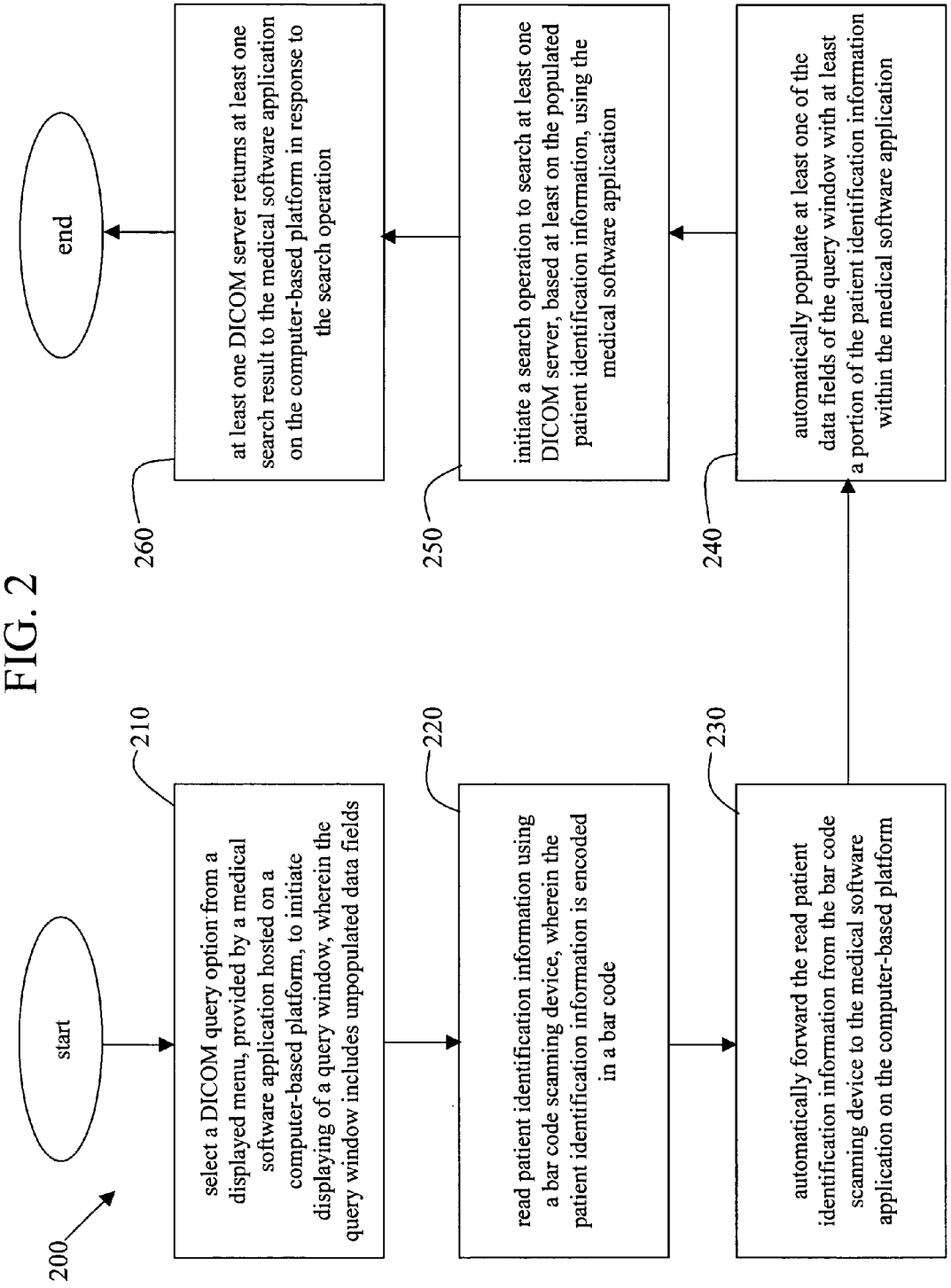
FIG. 2 is a flowchart of a first exemplary embodiment of a method to automatically generate a query to a DICOM server using the system of FIG. 1, in accordance with various aspects of the present invention.

FIG. 2 is a flowchart of an exemplary embodiment of a method 200 to automatically generate a query to a DICOM server (e.g., 110) using the system 100 of FIG. 1, in accordance with various aspects of the present invention. In step 210, a DICOM query option is selected from a displayed menu, provided by a medical software application hosted on a computer-based platform, to initiate displaying of a query window. The query window includes unpopulated data fields. In step 220, patient identification information is read using a bar code scanning device. The patient identification information is encoded in a bar code on, for example, a patient identification card belonging to a medical patient. In step 230, the read patient identification information is automatically forwarded from the bar code scanning device to the medical software application on the computer-based platform. In step 240, at least one of the data fields of the query window is automatically populated with at least a portion of the patient identification information within the medical software application. In step 250, a search operation is initiated to search at least one DICOM server, based at least on the populated patient identification information, using the medical software application. In step 260, at least one DICOM server returns at least one search result to the medical software application on the computer-based platform in response to the search operation.

Figure 3:
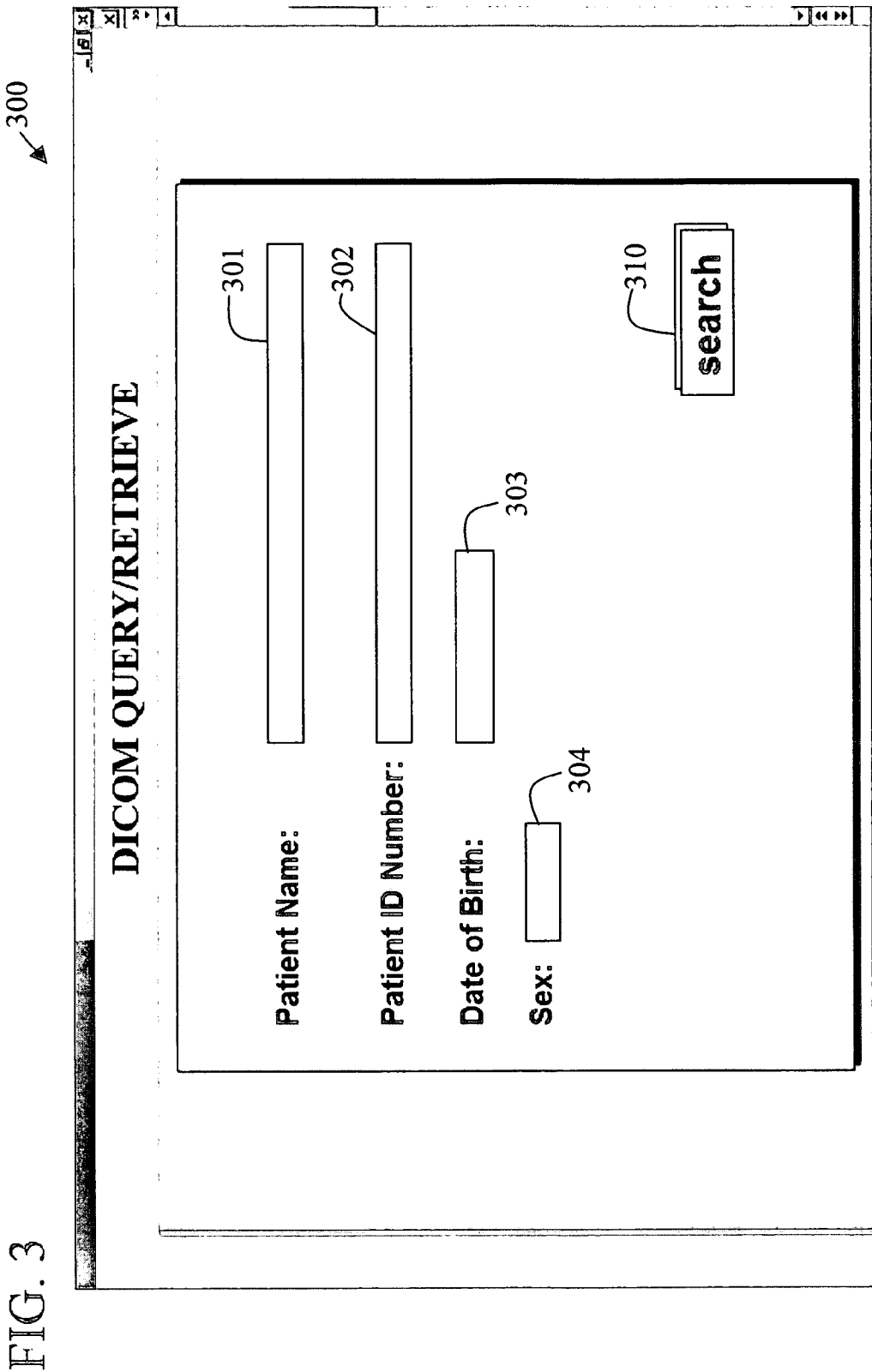
FIG. 3 illustrates a first exemplary embodiment of a query window displayed by the system of FIG. 1 as part of the method of FIG. 2, in accordance with various aspects of the present invention.

FIG. 3 illustrates a first exemplary embodiment of a query window 300 displayed by the system 100 of FIG. 1 as part of the method 200 of FIG. 2, in accordance with various aspects of the present invention. When a user of the system 100 selects a first type of DICOM query option from a displayed menu on the display 143, the DICOM query/retrieve window 300 (170 in FIG. 1) is displayed on the display 143. The DICOM query/retrieve window 300 includes several unpopulated data fields (e.g., 301-304). In FIG. 3, the unpopulated data fields 301-304 correspond to data entry locations for a patient name, a patient identification (ID) number, a date of birth, and sex. The DICOM query/retrieve window 300 also includes a search or query icon button 310. Other data fields and window configurations are possible as well, in accordance with various embodiments of the present invention.

Figure 4:
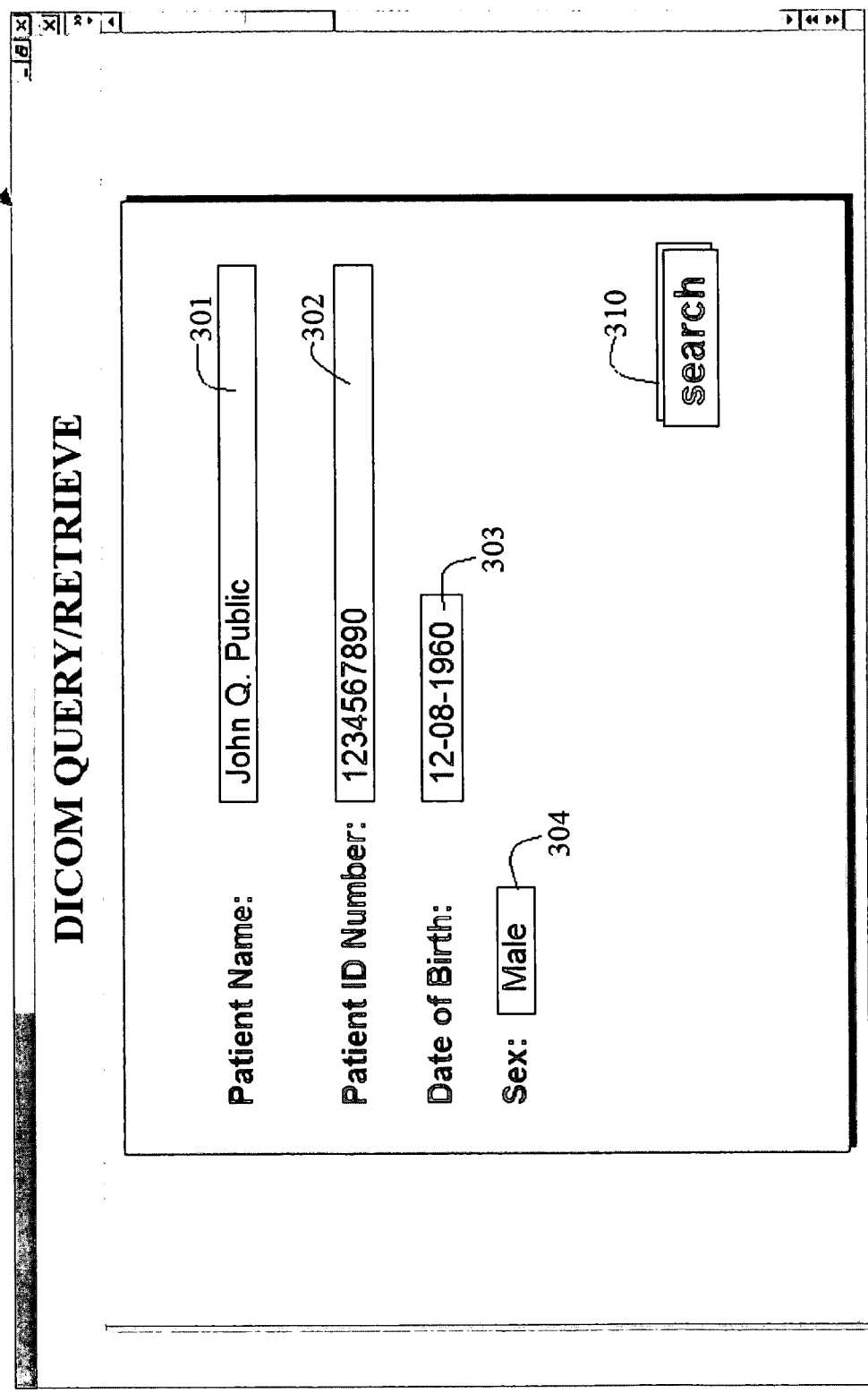
FIG. 4 illustrates the query window of FIG. 3 having data fields popuulated with exemplary patient information, in accordance with an embodiment of the present invention.

When the system 100 reads the encoded patient information from the patient identification card 120, the read patient information is forwarded to the computer-based platform 140 where the medical software application 145 takes the patient information and populates the appropriate data fields 301-304 with the corresponding patient information as shown in FIG. 4. The patient is a male named "John Q. Public" having a date of birth of Dec. 8, 1960 and a patient identification number of 1234567890. In accordance with an embodiment of the present invention, the patient identification number may include a social security number. In accordance with another embodiment of the present invention, the patient identification number may include an insurance number or any other type of patient identifying code.

Once the data fields are populated with the patient information, the user may select, using the user interface 142, the search button 310 to initiate a search operation (i.e., a DICOM query operation). In accordance with certain embodiments of the present invention, not all of the data fields need to be populated. That is, a search operation may be performed using some portion or subset of the read patient identification information. Also, in accordance with an alternative embodiment of the present invention, a user does not have to manually initiate the search operation by selecting the search button 310. Instead, the search operation may be automatically initiated by the medical software application 145 once the data fields are populated.

Furthermore, in accordance with yet another alternative embodiment of the present invention, the steps of displaying and populating a query window may be skipped altogether. Instead, the bar code scanning device 130 may read the patient identification information from the bar code 125 on the patient identification card 120 and a search operation may be automatically and immediately initiated by the medical software application 145 without displaying any of the patient identification information to the user beforehand.

For example, as part of the search operation, the patient information populated in the DICOM query/retrieve window 300 is used as search terms by the medical software application to search the DICOM server 110 via the network 150. As a result, a file of digital medical images corresponding to the patient "John Q. Public" is found and accessed from the image database 160 by the DICOM server 110. The DICOM server 110 then sends the file of digital medical images to the computer-based platform 140 via the network 150. The user may open the file and view the digital medical images using the computer-based platform 140. In accordance with certain embodiments of the present invention, the user may need to specify which DICOM server or servers to search, before initiating a search operation.

Figure 5:
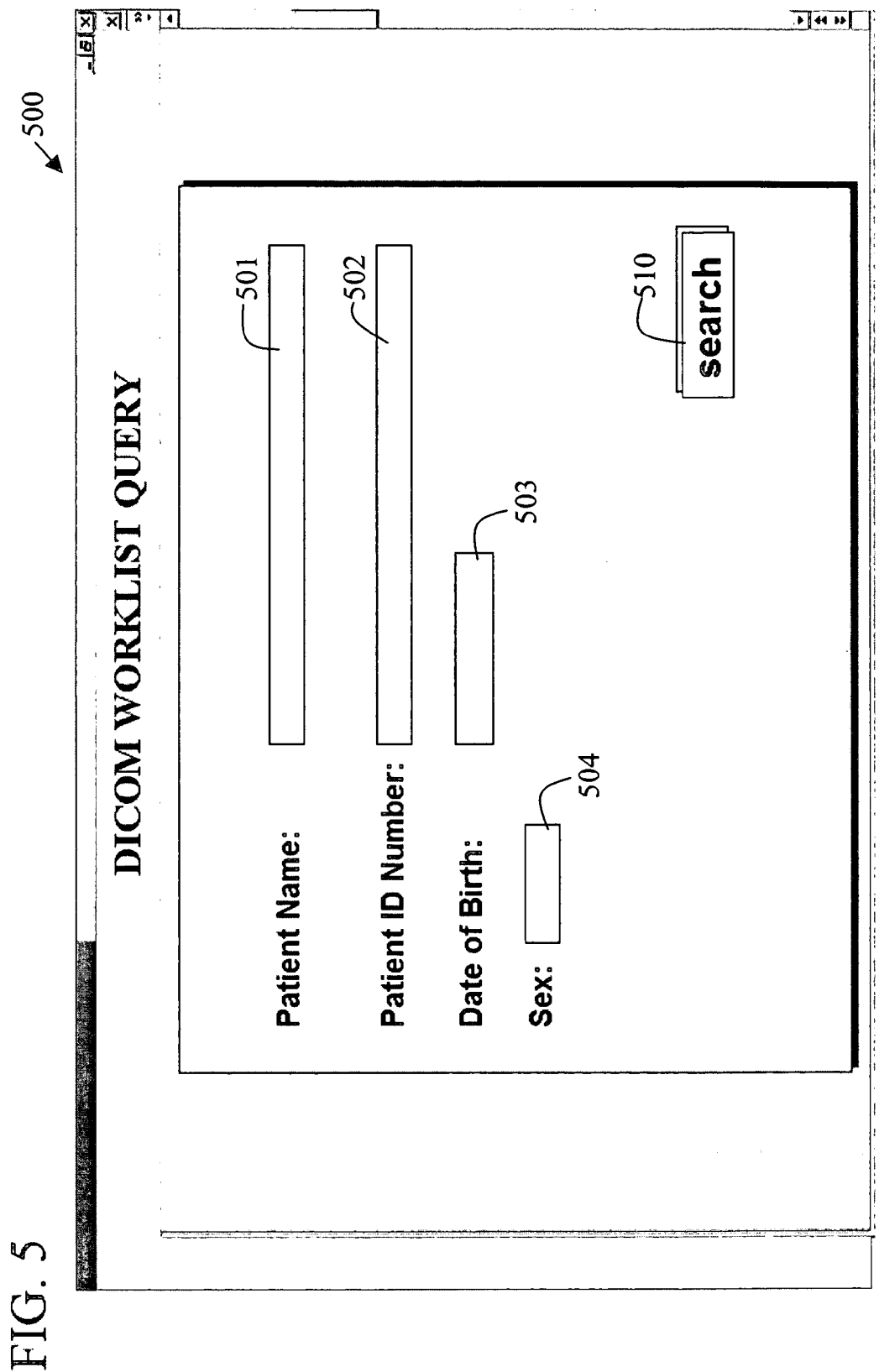
FIG. 5 illustrates a second exemplary embodiment of a query window displayed by the system of FIG. 1 as part of the method of FIG. 2, in accordance with various aspects of the present invention.

FIG. 5 illustrates a second exemplary embodiment of a query window 300 displayed by the system 100 of FIG. 1 as part of the method 200 of FIG. 2, in accordance with various aspects of the present invention. When a user of the system 100 selects a second type of DICOM query option from a displayed menu on the display 143, the DICOM worklist query window 500 (e.g., 170 in FIG. 1) is displayed on the display 143. The DICOM worklist query window 500 includes several unpopulated data fields (e.g., 501-504). In FIG. 5, the unpopulated data fields 501-504 correspond to data entry locations for a patient name, a patient identification (ID) number, a date of birth, and sex. The DICOM worklist query window 300 also includes a search or query icon button 510.

When the system 100 reads the encoded patient information from the patient identification card 120, the read patient information is forwarded to the computer-based platform 140 where the medical software application 145 takes the patient information and populates the appropriate data fields 501-504 with the corresponding patient information, similar to as shown in FIG. 4. Once the data fields are populated with the patient information, the user may select, using the user interface 142, the search button 510 to initiate a search operation (i.e., a DICOM query operation).

As an example, a worklist may comprise, for example, a digital file that lists instructions for carrying out an examination or imaging session for a particular patient. Alternatively, a worklist may comprise, for example, a list of all patients to be examined on a particular day using a particular medical imaging machine. Other worklists are possible as well, in accordance with various aspects of the present invention. A user of the system 100 may desire to access a worklist corresponding to a particular patient from the DICOM server 110 using the computer-based platform 140 by scanning a patient identification card 120 of the particular patient and generating a DICOM worklist query. In such a case, the DICOM server 110 may be serving as part of a Radiology Information System (RIS) at a hospital and the computer-based platform 140 may be serving as a workstation at an imaging clinic.

For example, as part of the search operation, the patient information populated in the DICOM worklist query window 500 is used as search terms by the medical software application 145 to search the DICOM servers 110-112 via the network 150. As a result, a worklist file corresponding to the patient "John Q. Public" is found and accessed by the DICOM server 111. The DICOM server 111 then sends the worklist file to the computer-based platform 140 via the network 150. The user may open the file and view the worklist using the computer-based platform 140. The user may then follow the instructions in the worklist to complete an examination on the patient, for example.

Figure 6:
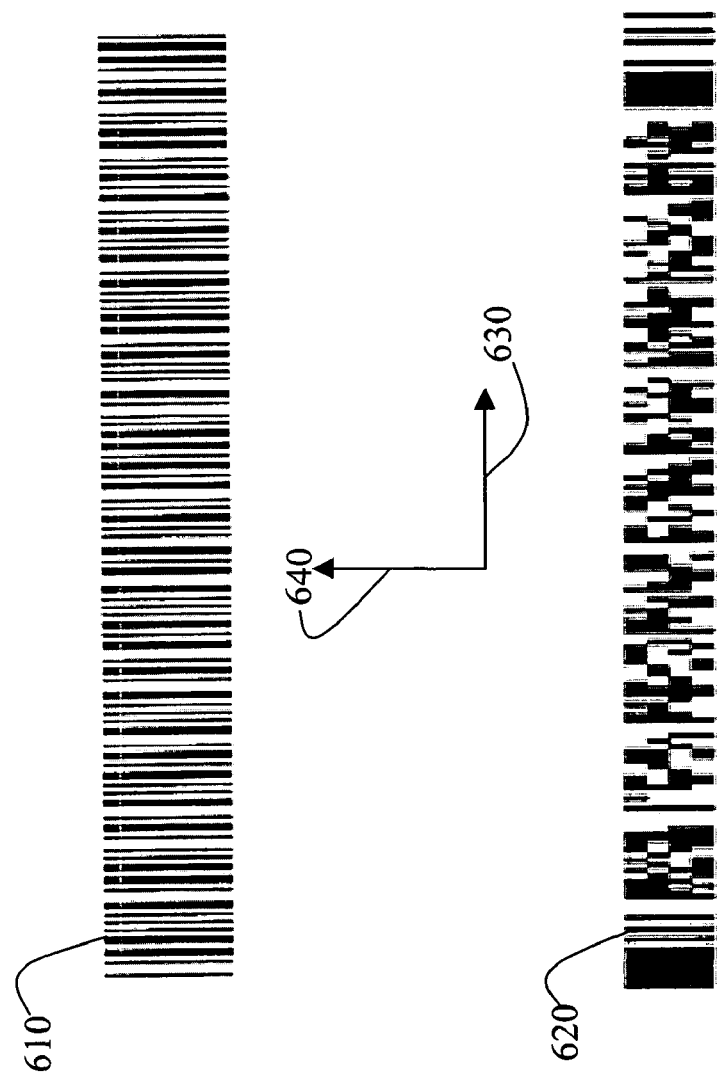
FIG. 6 illustrates exemplary embodiments of two types of bar codes that may be used on the patient identification card of the system of FIG. 1, in accordance with various aspects of the present invention.

FIG. 6 illustrates exemplary embodiments of two types of bar codes 610 and 620 that may be used on the patient identification card 120 of the system 100 of FIG. 1, in accordance with various aspects of the present invention. The bar code 610 is a one-dimensional bar code type that may be used to encode patient identification information along a first direction 630. The bar code 620 is a two-dimensional bar code type that may be used to encode patient identification information along both the first direction 630 and a second direction 640. Other bar code encoding schemes may be possible as well, in accordance with various embodiments of the present invention.

In accordance with certain alternative embodiments of the present invention, patient identification information may be encoded in other ways, other than bar code, on a patient identification card and may be read by an appropriate reader device, instead of a bar code scanner. For example, the patient identification card 120 may include an RF ID chip which is encoded with patient identification information according to RF ID standards (see FIG. 7). The bar code scanning device 130, in such a case, would be replaced with an RF ID interrogator/reader 730 operationally interfacing to the computer-based platform 140.

Figure 8:
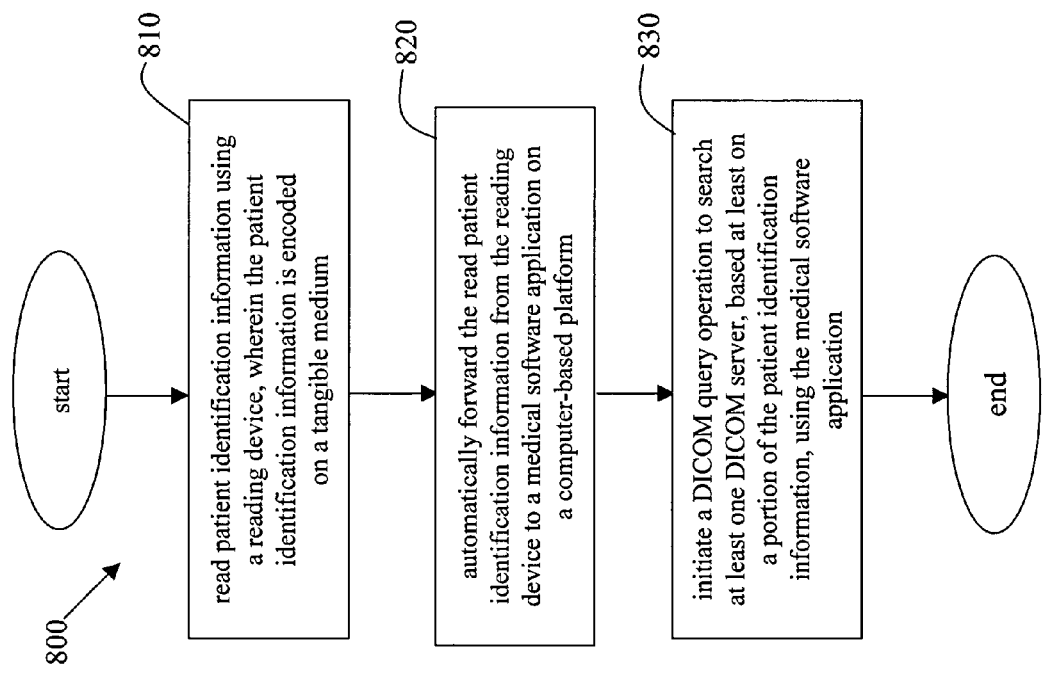
FIG. 8 is a flowchart of a second exemplary embodiment of a method to automatically generate a query to a DICOM server using the system of FIG. 1 or FIG. 7, in accordance with various aspects of the present invention.

FIG. 8 is a flowchart of a second exemplary embodiment of a method 800 to automatically generate a query to a DICOM server using the system 100 of FIG. 1 or FIG. 7, in accordance with various aspects of the present invention. In step 810, patient identification information is read using a reading device, wherein the patient identification information is encoded on a tangible medium. In step 820, the read patient identification information is automatically forwarded from the reading device to a medical software application on a computer-based platform. In step 830, a DICOM query operation is initiated to search at least one DICOM server, based at least on a portion of the patient identification information, using the medical software application.

In summary, embodiments of the present invention provide a system and method to for automatically generating a query to a DICOM server. A reading device is used to easily read patient identification information encoded on a tangible medium and automatically use the patient identification to perform a DICOM query operation (e.g., a DICOM query/retrieve or a DICOM worklist query). A medical software application hosted on a computer-based platform uses the read patient identification information as search criteria to perform the query operation. As a result, a user does not have to manually enter patient identification information before a query can be initiated.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. A method to automatically generate a query to a Digital Imaging and Communication in Medicine (DICOM) server, said method comprising:

selecting a DICOM query option from a displayed menu, provided by a patient management software application hosted on a personal computer, to initiate displaying of a query window, wherein said query window includes unpopulated data fields;

reading patient identification information using a radio frequency identification (RFID) scanning device, wherein said patient identification information is encoded in a RFID tag or chip;

automatically forwarding said read patient identification information from said RFID scanning device to said patient management software application on said personal computer;

automatically populating at least one of said data fields of said query window with at least a portion of said patient identification information within said patient management software application; and initiating a search operation to search at least one DICOM server, based at least on said populated patient identification information, for one or more of at least one medical image, at least one medical study, and at least one medical report using said patient management software application.

2. The method of claim 1 wherein said DICOM query option corresponds to a DICOM query/retrieve.

3. The method of claim 1 wherein said patient identification information includes at least one of a patient's name, a patient identification number, a patient's sex, a patient's date of birth, and a patient's age.

4. The method of claim 1 wherein said step of initiating a search operation is performed by a user of said patient management software application.

5. The method of claim 1 wherein said step of initiating a search operation is performed automatically by said patient management software application.

6. The method of claim 1 further comprising said at least one DICOM server returning at least one search result to said patient management software application on said personal computer in response to said search operation.

7. The method of claim 1 further comprising said at least one DICOM server returning at least one of a medical image, a medical study, and a medical report associated with said patient to said patient management software application on said personal computer in response to at least said search operation.

8. A system for automatically generating a query to a Digital Imaging and Communication in Medicine (DICOM) server computer, said system comprising:

a RFID tag or chip including encoded patient identification information of a patient;

a RFID scanning device adapted to read said patient identification information encoded in said RFID tag or chip;

a personal computer hosting a patient management software application, said personal computer operationally interfacing to said RFID scanning device to receive said read patient identification information from said RFID scanning device and to automatically generate a DICOM query, using said patient management software application, such that said DICOM query includes at least a portion of said patient identification information; and at least one DICOM server computer operationally interfacing to said personal computer to receive said DICOM query from said personal computer and to provide at least one of a medical image, a medical study, and a medical report to said personal computer in response to said DICOM query.

9. The system of claim 8 wherein said at least one DICOM server computer operationally interfaces to said personal computer via at least one network.

10. The system of claim 9 wherein said at least one network comprises at least one of a local area network (LAN), a wide area network (WAN), and a global informational network.

11. The system of claim 8 further comprising at least one image data base operationally interfacing to said at least one DICOM server computer and storing digital medical images.

12. The system of claim 8 wherein said personal computer includes a central processing unit, a user interface, and a display.

13. The system of claim 8 wherein said RFID tag or chip is affixed to or printed on one of a patient identification card, a patient file, and a patient image.

14. The system of claim 8 wherein said patient identification information includes at least one of a patient's name, a patient identification number, a patient's sex, a patient's date of birth, and a patient's age.

15. A method to automatically generate a query to a Digital Imaging and Communication in Medicine (DICOM) server computer, said method comprising:

reading patient identification information using a RFID scanning device, wherein said patient identification information is encoded on a RFID tag or chip;

automatically forwarding said read patient identification information from said RFID scanning device to a patient management software application on a personal computer; and initiating a DICOM query operation to search at least one DICOM server computer for one or more of a medical image, a medical study, and a medical report associated with a patient, based at least on a portion of said patient identification information, using said patient management software application.

16. The method of claim 15 wherein said DICOM query operation corresponds to a DICOM query/retrieve.

17. The method of claim 15 wherein said patient identification information includes at least one of a patient's name, a patient identification number, a patient's sex, a patient's date of birth, and a patient's age.

18. The method of claim 15 wherein said step of initiating a DICOM query operation is performed by a user of said patient management software application.

19. The method of claim 15 wherein said step of initiating a DICOM query operation is performed automatically by said patient management software application.

20. The method of claim 15 wherein said RFID tag or chip is affixed to or printed on one of a patient identification card, a patient file, or a patient image.

\* \* \* \* \*